US012156812B2

(12) United States Patent
Kaleta et al.

(10) Patent No.: US 12,156,812 B2
(45) Date of Patent: Dec. 3, 2024

(54) APPARATUS AND METHODS FOR A PROSTHETIC MITRAL VALVE HOLDER

(71) Applicant: St. Jude Medical, Cardiology Division, Inc., St. Paul, MN (US)

(72) Inventors: Richard Kaleta, Arden Hills, MN (US); Bradley Charles Knippel, Lino Lakes, MN (US); Ryan J. Nesler, Mounds View, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 467 days.

(21) Appl. No.: 17/723,604

(22) Filed: Apr. 19, 2022

(65) Prior Publication Data

US 2022/0354644 A1 Nov. 10, 2022

Related U.S. Application Data

(60) Provisional application No. 63/184,349, filed on May 5, 2021.

(51) Int. Cl.
*A61F 2/24* (2006.01)
*A61B 17/04* (2006.01)
*A61F 2/95* (2013.01)

(52) U.S. Cl.
CPC ........ *A61F 2/2439* (2013.01); *A61B 17/0467* (2013.01); *A61B 17/0469* (2013.01); *A61F 2/2409* (2013.01); *A61F 2/9517* (2020.05); *A61F 2230/0017* (2013.01)

(58) Field of Classification Search
CPC .... A61F 2/2439; A61F 2/2409; A61F 2/9517; A61F 2230/0017; A61B 17/0467; A61B 17/0469
See application file for complete search history.

(56) References Cited

U.S. PATENT DOCUMENTS

| | | | |
|---|---|---|---|
| 4,211,325 A * | 7/1980 | Wright | B65D 81/00 623/2.11 |
| 4,865,600 A | 9/1989 | Carpentier et al. | |
| 7,389,874 B2 * | 6/2008 | Quest | A61F 2/2427 206/363 |
| 8,273,118 B2 | 9/2012 | Bergin | |
| 8,398,707 B2 | 3/2013 | Bergin | |
| 9,289,293 B2 | 3/2016 | Murad et al. | |
| 9,333,076 B1 * | 5/2016 | Edquist | A61F 2/2427 |
| 10,463,485 B2 * | 11/2019 | Conklin | A61F 2/2439 |
| 10,722,356 B2 | 7/2020 | Conklin et al. | |

(Continued)

FOREIGN PATENT DOCUMENTS

WO 2016101529 A1 6/2016

*Primary Examiner* — Phong Son H Dang
(74) *Attorney, Agent, or Firm* — SLEMAN & LUND LLP

(57) ABSTRACT

A holder for a prosthetic heart valve includes a base having an annular portion defining an aperture, and a spool rotatably mated with the base. The spool has a platform and a head extending in a longitudinal direction from the platform. The holder further includes a button housing having an aperture sized and shaped to receive the head of the spool, and a button inserted in the button housing. The button housing is detachably coupled to the spool in an assembled condition. The button is movable relative to the button housing to move the button housing from a condition locked to the spool to a condition removable from the spool.

13 Claims, 10 Drawing Sheets

(56) References Cited

U.S. PATENT DOCUMENTS

| | | | | |
|---|---|---|---|---|
| 11,026,787 B2* | 6/2021 | Kaleta | ................... | A61F 2/2427 |
| 2002/0013621 A1* | 1/2002 | Stobie | ................... | A61F 2/2427 |
| | | | | 623/2.11 |
| 2012/0290079 A1* | 11/2012 | Murad | ................... | A61F 2/2412 |
| | | | | 623/2.17 |
| 2018/0116795 A1* | 5/2018 | Conklin | ................ | A61F 2/2427 |

* cited by examiner

APPARATUS AND METHODS FOR A PROSTHETIC MITRAL VALVE HOLDER

CROSS-REFERENCE TO RELATED APPLICATIONS

This application claims the benefit of the filing date of U.S. Provisional Application No. 63/184,349 filed May 5, 2021, the disclosure of which is hereby incorporated by reference herein in its entirety.

FIELD OF THE INVENTION

The present invention relates to prosthetic heart valves, and more particularly to apparatus for use in holding such valves prior to and during implantation of the valve in a patient.

BACKGROUND

Prosthetic heart valves are used for replacing diseased and/or deficient valves in a patient's heart. For example, a patient's mitral and/or aortic valves may need to be replaced by such prostheses. One illustrative type of prosthetic heart valve includes animal tissue that has been treated to make it suitable for long-term use in a patient's body. Prior to implantation, such tissue valves may need to be stored in a liquid that preserves the tissue and keeps it flexible. During the implantation procedure, the prosthetic tissue valve is removed from the storage liquid, rinsed extensively to remove any vestige of that liquid, and then implanted in the patient, typically in an "open heart" surgical procedure. In addition, during the implantation procedure, it may be desirable to temporarily modify the shape of the prosthetic tissue valve in certain respects in order to facilitate getting the valve into place in the patient with good visualization and with good access for suturing the valve to native tissue of the patient. For example, this temporary shape modification may include deflecting free end portions of the commissure posts of the prosthetic tissue valve radially inward. This shape modification is preferably done just prior to the implantation procedure to avoid any part of the valve taking an undesirable "set" during prolonged deformation.

The above aspects of prosthetic tissue valve handling may be aided by associating the valve with a so-called holder. This association may include a suture connection between the valve and the holder. The holder can be used to hold the valve in its storage liquid. When it is desired to use (implant) the valve, a handle can be removably attached to the holder to remove the holder and valve from the storage liquid and to hold those components during the above-described rinsing. Upon rinsing and/or sterilizing the holder and the prosthetic heart valve assembly, it can be difficult to access many surfaces of the components of a fully assembled holder and valve when there is little to no space between the components to access and clean the interior surfaces of the assembly. Attachment of the handle to the holder (or subsequent manipulation of the handle relative to the holder) may also be used to cause the above-described temporary deformation of the valve. The handle may also be used to place the holder and valve in the patient. The handle may be removed from the holder during suturing of the valve into the patient; however, visibility of the prosthetic valve may be decreased while suturing the valve to the patient due to the bulky parts of the holder left behind. The holder may be decoupled from the prosthetic valve by cutting each individual suture attaching the holder to the prosthetic valve in different locations.

From the foregoing it will be seen that efficient, easy, and reliable handle and holder attaching and detaching as well as effective cleaning of the valve and holder are highly desirable. Improvements to this aspect (and related aspects) of prosthetic heart valve apparatus are therefore sought. Among other advantages, the present disclosure may address one or more of these needs.

BRIEF SUMMARY

According to a first aspect of the disclosure, a holder for a prosthetic heart valve includes a base, a spool, a button housing and a button. The base may have an annular portion defining an aperture. The spool may include a platform and a head extending in a longitudinal direction from the platform, and may be rotatably mated with the base. The button housing may have an aperture sized and shaped to receive the head of the spool, and may be detachably coupled to the spool in an assembled condition. The button may be inserted into the button housing. The button may have a button aperture sized and shaped to receive the head of the spool.

According to another aspect of the disclosure, a kit for a prosthetic heat valve assembly may include a prosthetic heart valve, a prosthetic heart valve holder, and a handle. The prosthetic heart valve may have a frame extending circumferentially about a longitudinal axis and surrounding a central opening, a plurality of leaflets disposed in the central opening and affixed to the frame, each adjacent pair of leaflets together defining a commissure, and a sewing cuff affixed to the frame and extending circumferentially about an exterior of the frame. The prosthetic heart valve holder may include a base, a spool, and a button housing. The base may have an annular portion defining an aperture. The spool may be rotatably connectable to the base, and may include a platform and a head extending from the platform. The button housing may have an aperture sized and shaped to receive the head of the spool, and may be detachably couplable to the spool. The handle may be connectable to the button housing of the prosthetic heart valve holder, and may be releasable from the prosthetic heart valve assembly in combination with the button housing.

According to another aspect of the disclosure, a method of implanting a prosthetic heart valve in a patient may include coupling a handle to a first portion of a prosthetic heart valve assembly by rotating the handle relative to the prosthetic heart valve assembly, the prosthetic heart valve assembly including a prosthetic heart valve and a holder coupled to the prosthetic heart valve by a plurality of sutures, the prosthetic heart valve having a frame, a plurality of leaflets joined to the frame, and a sewing cuff surrounding the frame, and the holder including the first portion of the prosthetic heart valve assembly that is releasable from a remainder of the prosthetic heart valve assembly; further rotating the handle relative to the prosthetic heart valve assembly to deflect the frame of the prosthetic heart valve; positioning the prosthetic heart valve in a native heart valve annulus of the patient; decoupling the handle and the first portion of the prosthetic heart valve assembly from the remainder of the prosthetic heart valve assembly; suturing the sewing cuff of the prosthetic heart valve to the native heart valve annulus; cutting the plurality of sutures at a single location to decouple the holder from the prosthetic heart valve; and removing the holder from the patient.

BRIEF DESCRIPTION OF THE DRAWINGS

A more complete appreciation of the subject matter of the present disclosure and the various advantages thereof can be realized by reference to the following detailed description in which reference is made to the accompanying drawings in which.

DETAILED DESCRIPTION

As used herein in connection with devices for delivering a prosthetic heart valve or other medical device into a patient, the terms "proximal" and "distal" are to be taken as relative to the user of the delivery devices (e.g., a surgeon). "Proximal" is to be understood as relatively close to the user, and "distal" is to be understood as relatively farther away from the user. Also as used herein, the terms "generally," "substantially," "approximately," and "about" are intended to mean that slight deviations from absolute are included within the scope of the term so modified.

When used to indicate relative locations within the prosthetic heart valve, the terms "longitudinal" and "vertical" are to be taken as the direction of the axis extending between the inflow end and the outflow end of the stent of the heart valve, along the direction of intended blood flow; and the term "flow direction" is to be taken as the direction from the inflow end to the outflow end of the stent of the heart valve along the direction of intended blood flow. In the prosthetic heart valve and holder assembly described herein, the inflow end of the valve is the proximal end of the valve and the outflow end is the distal end of the valve when the valve is oriented for implantation. A handle of the valve holder, as described below, is positioned at the proximal end of the holder to be grasped by a user, and a base of the valve holder is positioned at the distal end of the holder when the holder is oriented for implantation. When used to indicate relative locations within the prosthetic heart valve assembly, the term "circumferential" is to be taken as the direction of rotation about the longitudinal axis of the heart valve frame.

Figure 1:
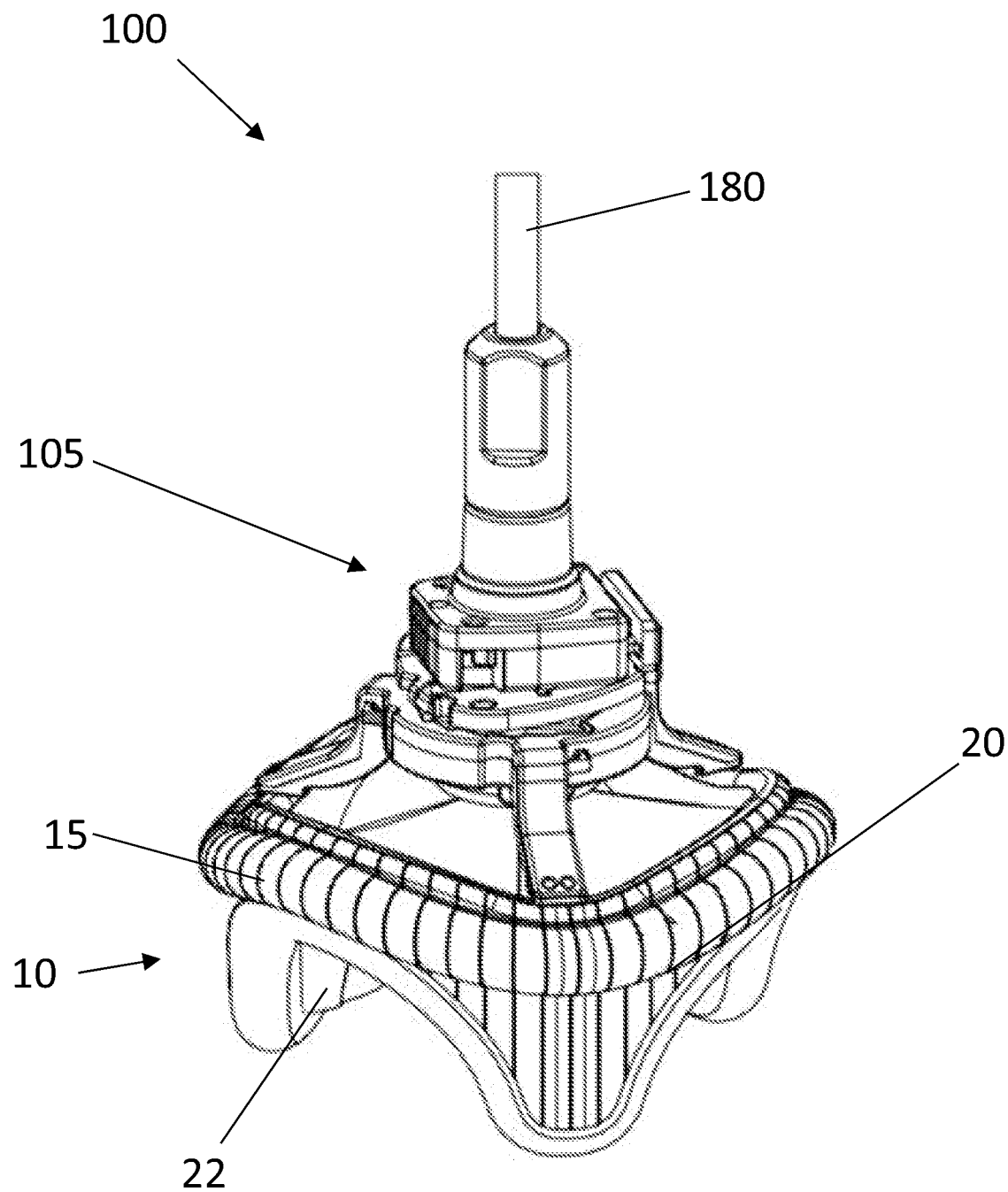
FIG. 1 is a perspective view of a prosthetic heart valve and holder assembly according to an embodiment of the disclosure.

As described herein, "prosthetic heart valve assembly" is used to refer to a prosthetic heart valve coupled to a prosthetic heart valve holder. FIG. 1 illustrates a prosthetic heart valve assembly 100 including valve holder 105 holding a prosthetic heart valve 10. As shown, a handle 180 may represent a proximal end of prosthetic heart valve assembly 100, the handle being configured to be grasped by a user (e.g., a surgeon), and prosthetic heart valve 10 may represent a distal end of the assembly. Prosthetic heart valve 10 is designed to replace a native valve of a patient, such as the pulmonary, mitral, tricuspid, or aortic valve. Prosthetic heart valve 10 may be implanted in a patient whose heart has been stopped, via a thoracotomy or open-heart surgery, for example. Prosthetic heart valve 10 may have a rigid frame (e.g., made of titanium or polymer) encapsulated by a cover 20 made, for example, from polyester fabric or tissue. A sewing cuff 15 at an inflow end of cover 20 may encapsulate a flexible ring (e.g., made of silicone) extending circumferentially about the exterior of the rigid frame in a closed curve shape (e.g., a circle). Alternatively, sewing cuff 15 may be replaced with a braided suture, for example, on a prosthetic aortic or mitral valve. Prosthetic heart valve 10 may have three leaflets 22 (e.g., made of bovine pericardial tissue or porcine cusps) that coapt in a central area of the prosthetic heart valve. Prosthetic heart valve 10 may be configured to be sewn into the native mitral annulus of the patient after removal of the patient's native mitral valve leaflets, with sewing cuff 15 positioned adjacent the native mitral annulus of the patient, and suturing may be used to stitch the sewing cuff to the native mitral annulus. The user may place the suturing circumferentially about sewing cuff 15 between the sewing cuff and the native mitral annulus, using a single or multiple continuous sutures, mattress sutures or a plurality of interrupted sutures. For example, three sutures may be used in an embodiment including multiple continuous sutures, each of the three sutures extending around part of the circumference of sewing cuff 15.

Figure 2:
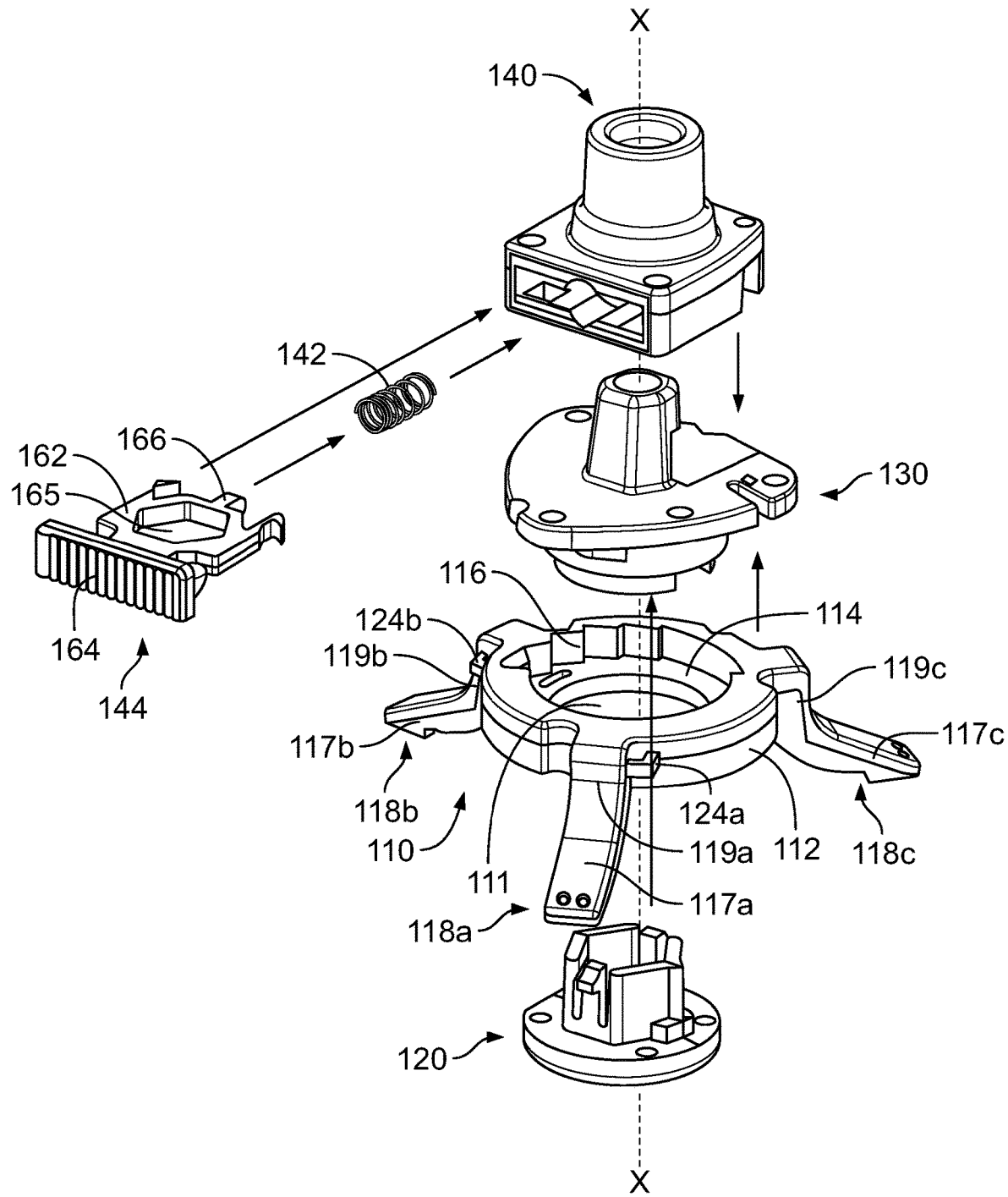
FIG. 2 is an exploded view of a prosthetic heart valve holder according to an embodiment of the disclosure.

The components of valve holder 105 are more clearly illustrated in FIG. 2, and include a base 110, a plug 120, a suture holding component such as a spool 130, a button housing 140, a spring 142 and a button 144. Valve holder 105 may be made of a rigid plastic material such as Ultem® or polysulfone, for example. It is contemplated that different components of valve holder 105 may be made of different materials.

Figure 3:
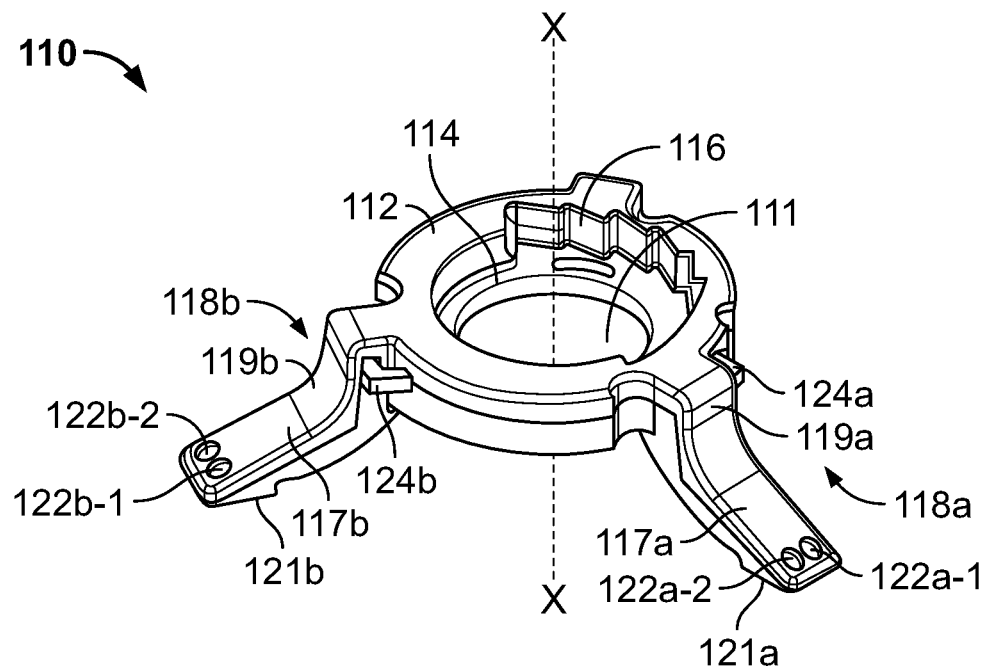
FIG. 3 is a perspective view of a base of the prosthetic heart valve holder of FIG. 2.

Base 110 is shown in FIGS. 2 and 3 according to an embodiment of the disclosure. Base 110 includes annular portion 112 extending circumferentially about longitudinal axis X. An interior lip 114 extends radially inward from the distal end of annular portion (i.e., lower on the page) and defines an aperture 111 through base 110. Interior lip 114 forms an annular platform for spool 130 to contact and rest on when the spool is coupled to base 110. A plurality of interior ridges 116 are located circumferentially around the interior proximal end of annular portion 112 (i.e., higher on the page). Ridges 116 are sized and shaped to engage with spool 130 when the spool is coupled to base 110. Ridges 116 may allow for rotation of spool 130 relative to base 110 about longitudinal axis X in a first direction (e.g., clockwise), while preventing rotation of the spool relative to the base in a second direction opposite the first direction (e.g., counterclockwise). Ridges 116 may be part of a ratcheting mechanism used to deflect stent posts of valve 10 medially, as described further below. Base 110 further includes a first leg 118a, a second leg 118b and a third leg 118c coupled to annular portion 112. Each leg 118a-c has an upper leg portion 119a, 119b, 119c, respectively, extending substantially parallel to longitudinal axis X, and a lower leg portion 117a, 117b, 117c, respectively, extending radially outward and in a distal (i.e., downward) direction from the upper leg portion to a terminal end. The terminal ends of lower leg portions 117a-c include downward facing surfaces 121a, 121b, 121c (121c is not shown), respectively, lying in a plane perpendicular to longitudinal axis X such that each leg 118a-c may rest stably on a surface, particularly another flat surface perpendicular to the longitudinal axis (e.g., a table).

Figure 8:
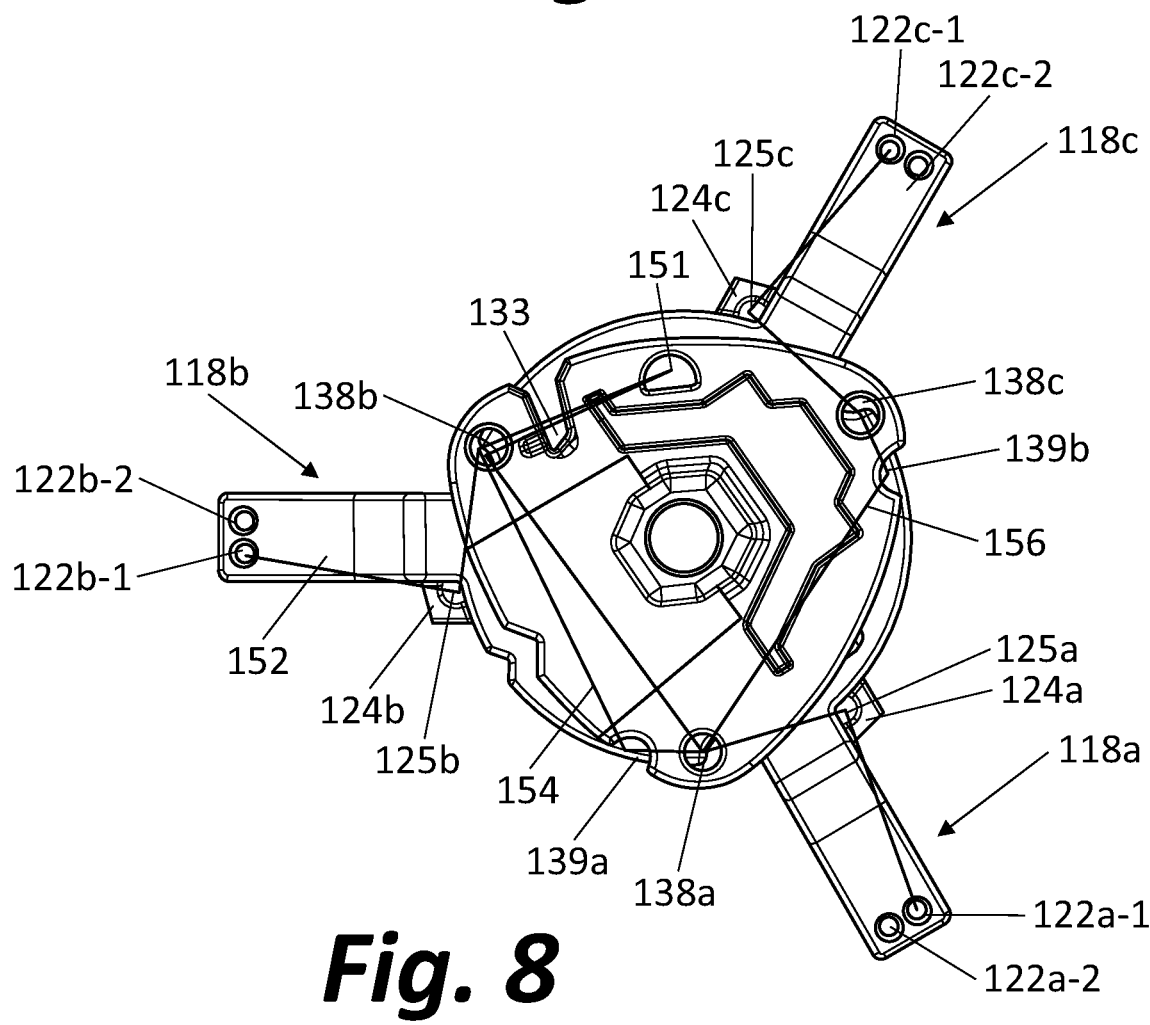

Each lower leg portion 117a-c further includes a pair of apertures proximate to the terminal end for securing sutures to valve holder 105, as is discussed further below. That is, first lower leg portion 117a includes suture anchors 122a-1 and 122a-2, second lower leg portion 117b includes suture anchors 122b-1 and 122b-2, and third lower leg portion 117c includes suture anchors 122c-1 and 122c-2, as shown in FIGS. 3 and 8. Further included on base 110 are tabs, each having an eyelet through which suture may be passed. For example, a first tab 124a may be positioned at the intersection of upper leg portion 119a and the exterior surface of annular portion 112. Tab 124a includes an eyelet 125a most clearly shown in FIG. 8. A second tab 124b positioned at the intersection of upper leg portion 119b and the exterior surface of annular portion 112 includes an eyelet 125b, and a third tab 124c positioned at the intersection of upper leg portion 119c and the exterior surface of annular portion 112 includes an eyelet 125c.

Figure 4:
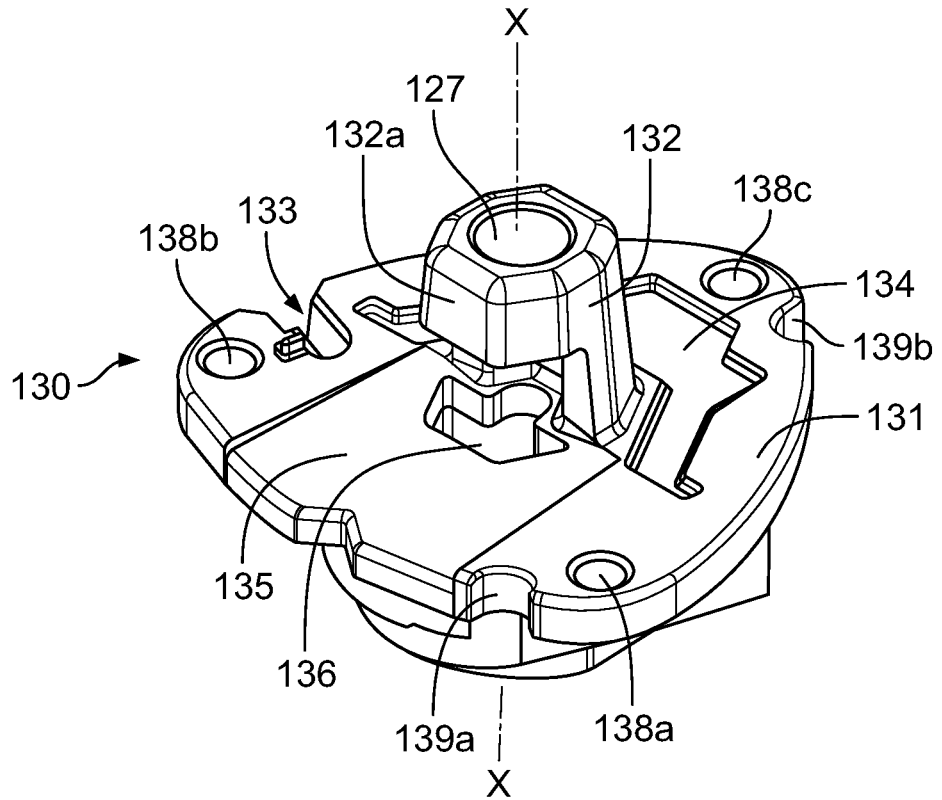
FIG. 4 is a perspective view of a spool of the prosthetic heart valve holder of FIG. 2.

FIG. 4 illustrates spool 130 according to an embodiment of the disclosure, the spool being configured to mate at least with base 110. Spool 130 includes a platform 131 surrounding longitudinal axis X and a head 132 protruding generally proximally from the center of the platform along the longitudinal axis. Head 132 tapers as the head extends proximally from platform 131 and may have a generally hexagonal transverse cross-section. Head 132 includes an enlarged recess in one side of the heading from its base to a position spaced from the proximal tip, forming an overhang 132a, and the head defines an aperture 127 size and shaped to receive handle 180, as will be discussed below in greater detail. An enlarged notch 133 in the perimeter of platform 131 provides an area that facilitates the cutting of sutures attaching valve 10 to valve holder 105. A proximal face of platform 131 has a partial impression 134 located substantially on a first side of head 132 and extending approximately halfway around a perimeter of the head. Opposite impression 134, platform 131 further includes a ramp 135 on its proximal face that extends from the base of head 132 in a radially outward and slightly distal (downward) direction, such that the surface of the ramp tapers relative to the surrounding platform face as the ramp extends outward. Impression 134 and ramp 135, together with an aperture 136 centrally located in platform 131, provide gaps and spaces between spool 130 and button housing 140 when valve holder 105 is in an assembled configuration. Gaps and spaces between components of valve holder 105 promote sterilization by allowing a chemical sterilant to penetrate a greater surface area of the valve holder. The gaps and spaces, such as aperture 136, further limit or prevent the formation of air bubbles when, for example, valve holder 105 is submerged in a pool of liquid to be cleaned and/or sterilized.

A plurality of apertures and indentation and/or recesses may be provided in various locations on or near the perimeter of platform 131 for receiving sutures that may be used to secure valve holder 105 to prosthetic heart valve 10. For example, the illustrated embodiment includes suture apertures 138a, 138b and 138c, as well as suture recesses 139a and 139b. Spool 130 may include additional apertures and/or recesses that are not visible in FIG. 4, such as suture anchor 151 shown in FIG. 8.

Figure 5A:
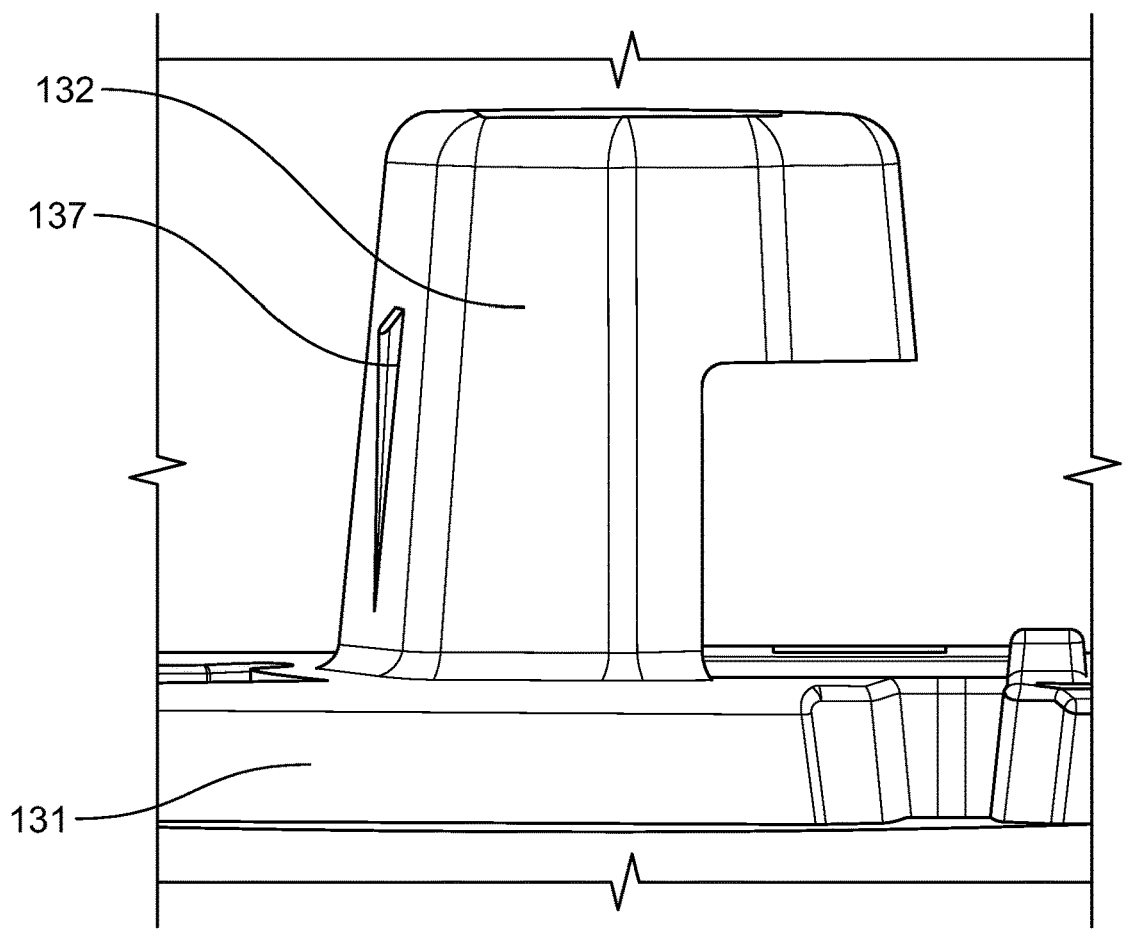
FIGS. 5A-5B are side and front elevational views, respectively, of the spool of FIG. 4.
Figure 5B:
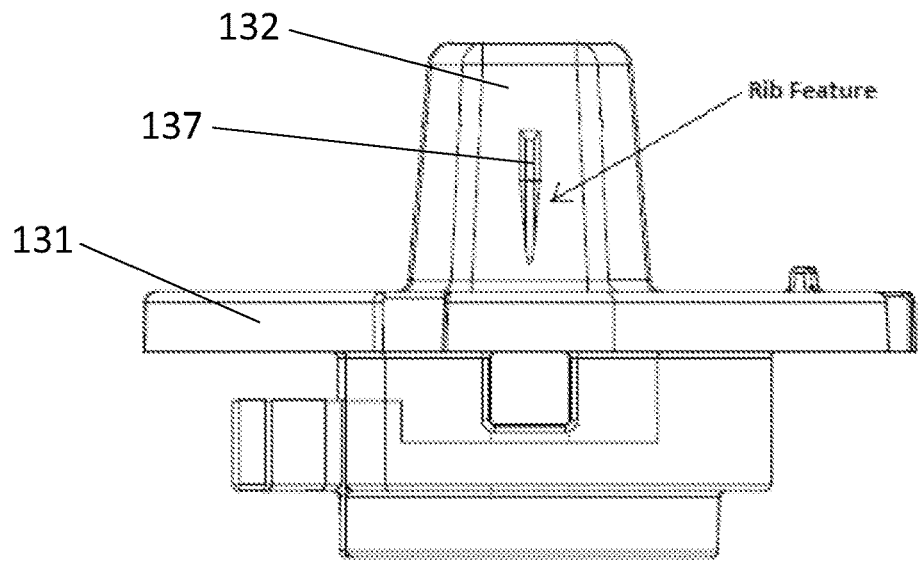

Spool 130 may further include a stability component such as rib 137, as shown in FIGS. 5A-5B. Rib 137 is an elongate protrusion extending from a side of head 132. In the illustrated embodiment, rib 137 extends from the side of head 132 opposite the overhang formed by the proximal (upper) portion of the head, however, it is contemplated that the rib may extend from any side of the head. Rib 137 may protrude from head 132 generally in a radially outward direction, and the elongation of rib 137 may extend generally in the proximal-distal direction, however, any shape is contemplated for the rib. The addition of rib 137 may improve the stability of valve holder 105 when button housing 140 is assembled to spool 130, as will be described in more detail below.

Figure 7:
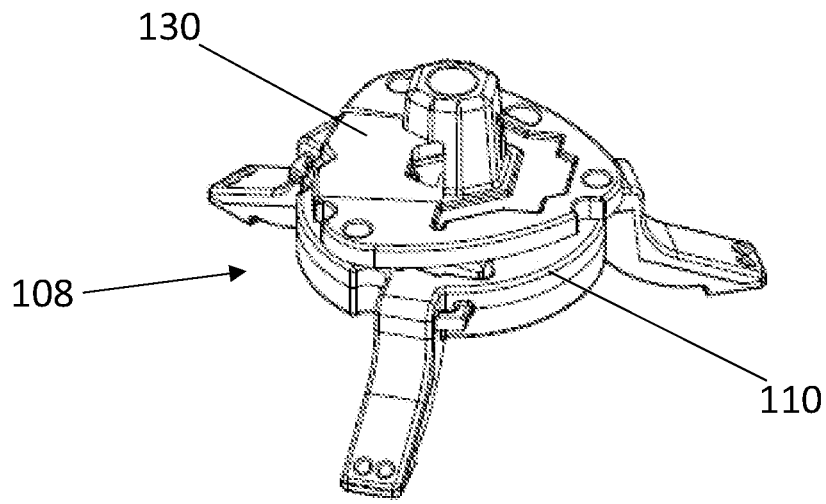
FIGS. 7-8 are perspective and top plan views, respectively, of an assembly of the base, spool and plug of the prosthetic heart valve holder of FIG. 2, with the plug not being visible.

FIGS. 7-8 illustrate spool 130, base 110 and plug 120 (not shown) coupled to one another in the assembled configuration, forming a base assembly 108. FIG. 8 further illustrates the sutures that couple spool 130 and base 110 to prosthetic heart valve 10 in the assembled configuration. Valve holder 105 may include a plurality of sutures extending through and/or around spool 130. In the embodiment illustrated in FIG. 9, spool 130 includes a first length of suture 152, a second length of suture 154 and a third length of suture 156. Each length of suture 152, 154, 156 is coupled (e.g., tied) to suture anchor 151 located on platform 131 of spool 130. Suture anchor 151 is illustrated as an aperture extending through platform 131, however, the suture anchor may be any useful means for tying a suture to the platform, such as a protrusion having an eyelet. Each length of suture 152, 154, 156 extends from suture anchor 151 to second suture aperture 138b, passing over notch 133. Passing each length of suture 152, 154, 156 over notch 133 enables the user to cut all three sutures in one location and potentially with the use of a single cut.

Figure 9:
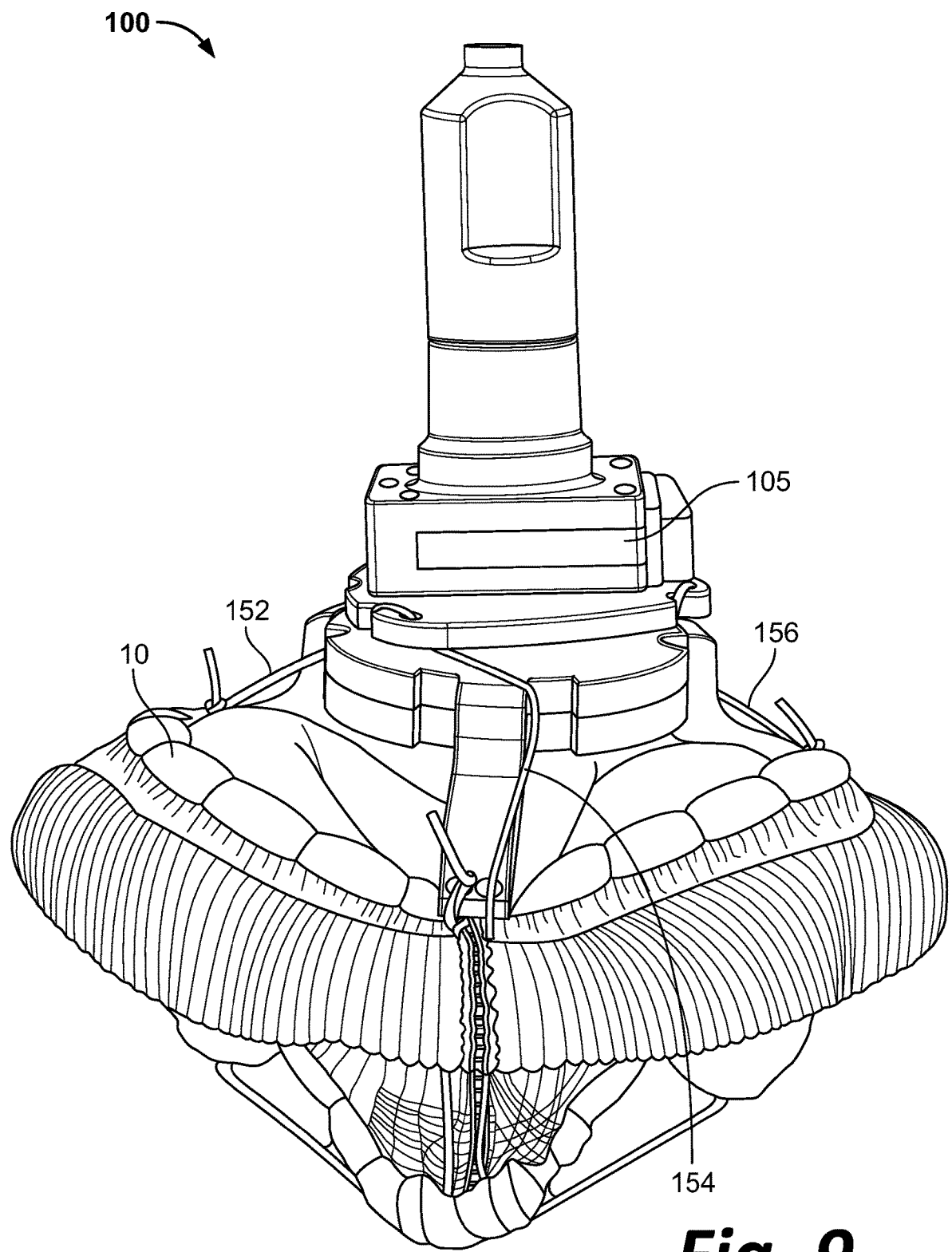
FIG. 9 is a perspective view of a prosthetic heart valve and holder assembly according to an embodiment of the disclosure.

Each length of suture 152, 154, 156 may extend in a different direction from second suture aperture 138b to couple to different locations of base 110 and form a stable attachment. In the illustrated embodiment, first length of suture 152 may extend from second suture aperture 138b, through eyelet 125b in tab 124b and from there toward the terminal end of second leg 118b to anchor to suture anchors 122b-1, 122b-2. First length of suture 152 may pass distally (downwardly) through a first suture anchor 122b-1 of second leg 118b and through a portion of prosthetic heart valve 10, and then proximally (upwardly) through the portion of the prosthetic heart valve to couple to a second suture anchor 122b-2, as shown in FIG. 9.

Second length of suture 154 may extend from second suture aperture 138b through first suture recess 139a and from there to first suture aperture 138a. After passing through first suture aperture 138a, second length of suture 154 may extend through eyelet 125a in tab 124a and toward the terminal end of first leg 118a to anchor to suture anchors 122a-1, 122a-2. Second length of suture 154 may couple to first leg 118a in a substantially similar manner as first length of suture 152. That is, the second length of suture may pass distally through a first suture anchor 122a-1 of first leg 118a and through a portion of prosthetic heart valve 10, and then proximally through the portion of the prosthetic heart valve to couple to a second suture anchor 122a-2 of the first leg.

Third length of suture 156 may extend distally through second suture aperture 138b, and proximally through second suture aperture 138a. Third length of suture 156 may then pass through second suture recess 139b and third suture aperture 138c, through eyelet 125c in tab 124c, and then toward the terminal end of third leg 118c. Third length of suture 156 may couple to leg 118c in a substantially similar manner as first and second lengths of suture 152, 154 couple to their respective legs. More particularly, the third length of suture may pass distally through a first suture anchor 122c-1 of third leg 118c and through a portion of prosthetic heart valve 10, and then proximally through the portion of the prosthetic heart valve to couple to a second suture anchor 122c-2 of the third leg.

Figure 10:
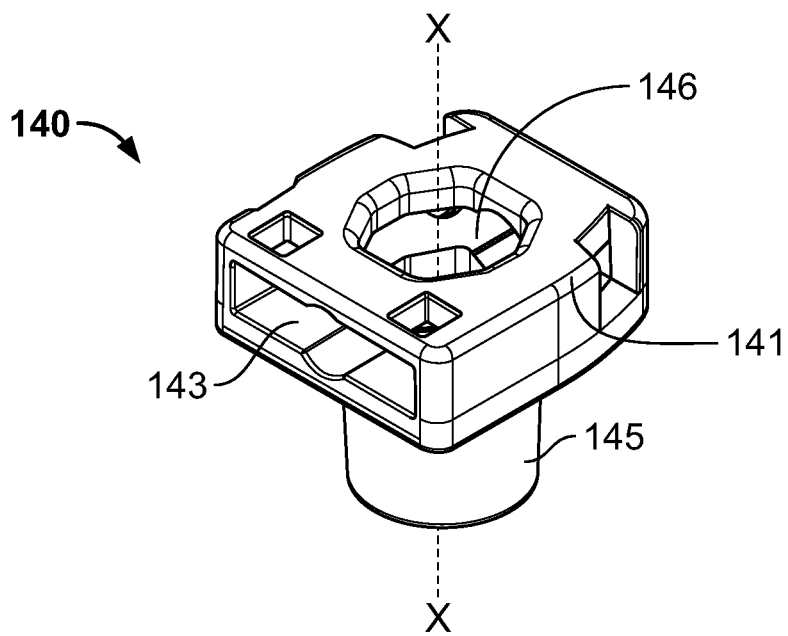
FIG. 10 is a perspective view of a button housing of the prosthetic heart valve holder of FIG. 2
Figure 11:
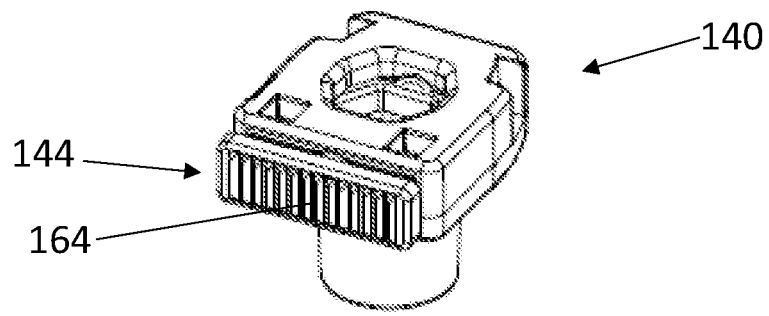
FIG. 11 is a perspective view of the button housing of FIG. 10 with a button inserted therein over a spring.

FIG. 10 shows an enlarged view of button housing 140 according to an embodiment of the disclosure. Button housing 140 includes a receiver 141, which is generally rectangular and configured to receive button 144. Receiver 141 is at least partially enclosed on all sides except one, on which the receiver defines a slot 143. Button 144 may be inserted into receiver 141 through slot 143, as shown in FIG. 11. Receiver 141 has a longitudinal aperture 146 extending along longitudinal axis X and located generally in the center of the receiver. Button housing 140 further includes a hollow stem 145 extending distally from receiver 141 along longitudinal axis X. Stem 145 defines a lumen which may be aligned with aperture 146 of receiver 141. As shown in FIG. 2, button 144 includes a frame 162 coupled to an actuator portion 164. An aperture 165 substantially in the center of frame 162 may be hexagonal in shape, although any shape that corresponds to the apertures of other components of valve holder 105 is contemplated. Frame 162 includes a tab 166 extending from a position on the frame opposite actuator portion 164. Tab 166 is configured to receive spring 142 when valve holder 105 is in an assembled configuration and button 144 is inserted into button housing 140. That is, one side of spring 142 may abut frame 162 surrounding tab 166, and the opposite side of the spring may abut the interior of button housing 140 when valve holder 105 is assembled. Spring 142 may be at least partially compressed in the assembled configuration, and therefore applying a biasing force upon button 144 in the direction out from slot 143. The bias of spring 142 may cause aperture 165 of button 144 to be out of concentric alignment with aperture 146 of receiver 141. When valve holder 105 is being assembled, button housing 140 may be positioned over spool 130 such that head 132 is inserted into aperture 146 of receiver 141, and the taper of head 132 may push button 144 transversely so that the apertures become aligned, further compressing spring 142. As button housing 140 is moved distally along head 132, frame 162 of button 144 will distally pass overhang 132a and reach the enlarged recess in the head, allowing spring 142 to push the button transversely beneath the overhang to lock the button housing to the head. In other words, the proximal face of frame 162 of button 144 may abut the distal face of overhang 132a, thereby placing the button in a locked condition and preventing the decoupling of button housing 140 from spool 130 when the button is at rest in the assembled configuration.

Figure 6:
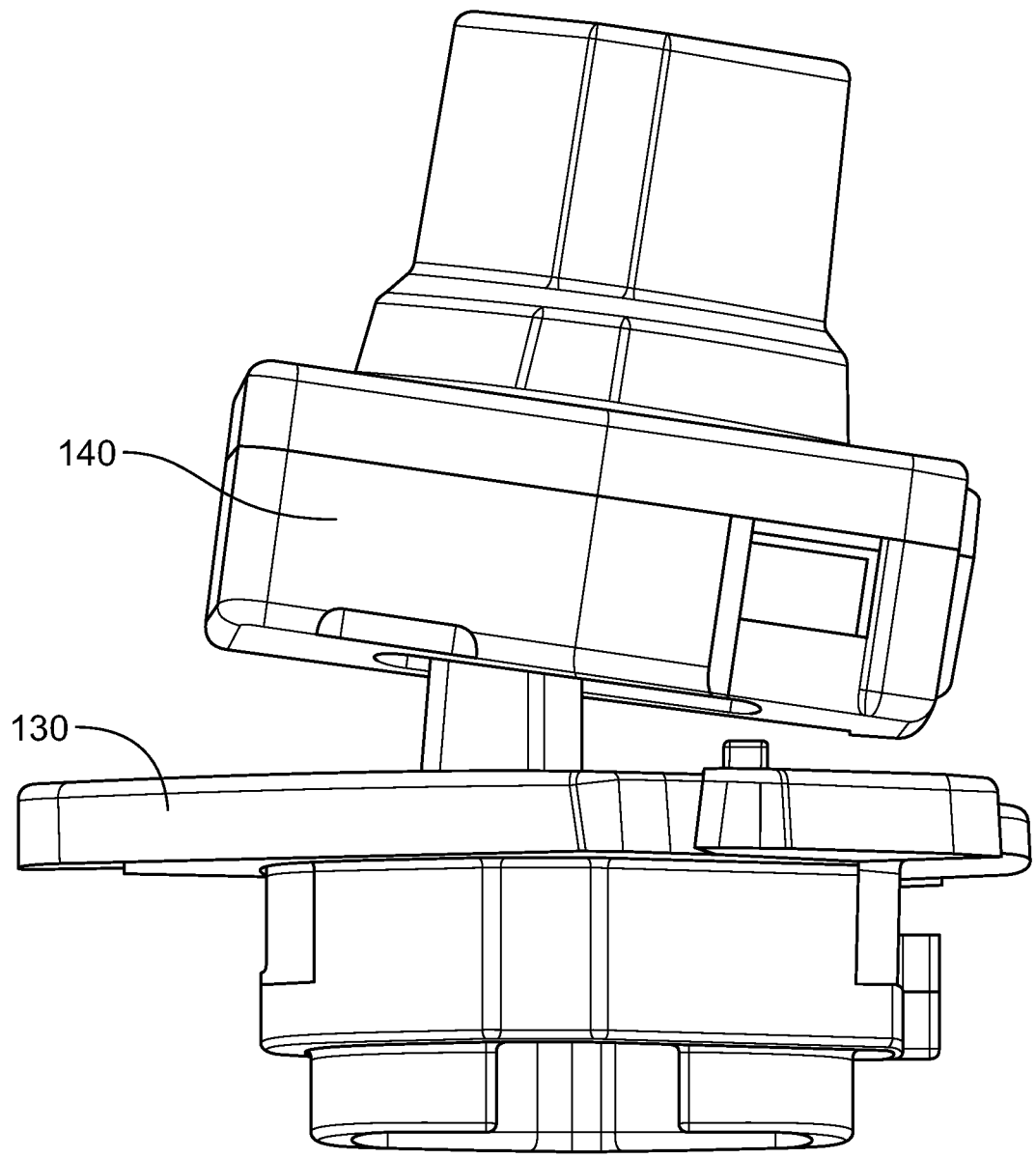
FIG. 6 is a side elevational view of a spool engaging with a button housing of the prosthetic heart valve holder of FIG. 2.

When button housing 140 is coupled to spool 130 in the assembled configuration, rib 137 may engage with the button housing to promote the stability of valve holder 105 by reinforcing head 132 to counteract bending moments applied to the valve holder and prevent the button housing from slipping off and/or detaching from the head of the spool. For example, FIG. 6 illustrates valve holder 105 in a condition with a bending moment applied to button housing 140 relative to spool 130. Rib 137 may assist in maintaining the coupling of button housing 140 to spool 130 in such a condition. The addition of rib 137 may improve the stability of valve holder 105 without increasing the size and/or radial thickness of head 132 of spool 130 around the entire perimeter of the head, allowing for the existence of various gaps and spaces within the valve holder to promote sterilization as described above.

Figure 12:
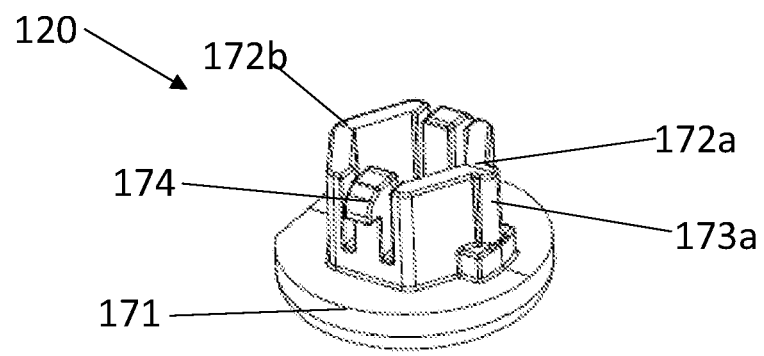
FIG. 12 is a perspective view of a plug of the prosthetic heart valve holder of FIG. 2.

FIG. 12 illustrates an enlarged view of plug 120. Plug 120 has a base 171 and walls extending proximally from the base. A first pair of walls 172a are connected to one another along a linear joint 173a, with each wall extending from the linear joint at an angle transverse to the other wall. A second pair of walls 172b are connected to one another along a linear joint (not shown, but substantially similar to linear joint 173a), the second pair of walls forming a mirror image opposite the first pair of walls 172a. Plug 120 further includes coupling components, such as latches 174, which oppose each other and extend from base 171 between and on both sides of first and second pairs of walls 172a and 172b. Walls 172a, 172b and latches 174 collectively define a substantially hexagonal interior space of plug 120, the distal end of the space being closed by base 171 and the proximal end being open. Latches 174 have a lip which connects plug 120 to spool 130 such that the plug and the spool may be rotated together about longitudinal axis X relative to base 110 when valve holder 105 is in the assembled configuration.

Figure 13A:
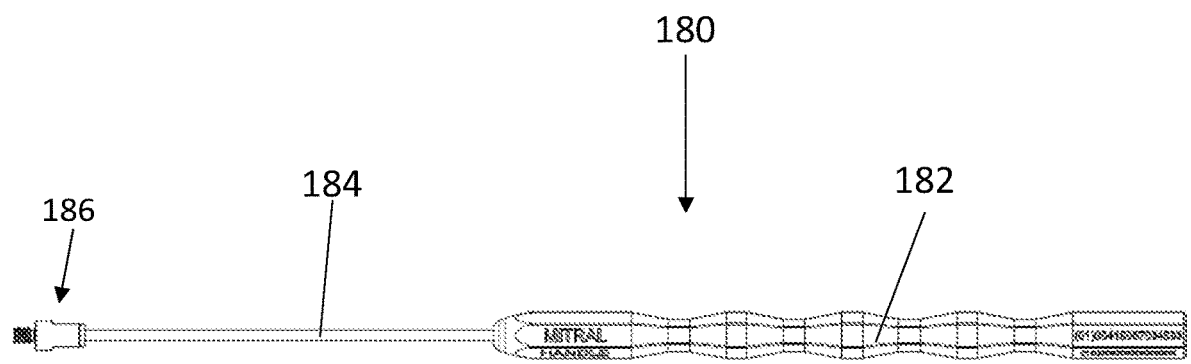
FIG. 13A is a side elevational view of a handle according to an embodiment of the disclosure.
Figure 13B:
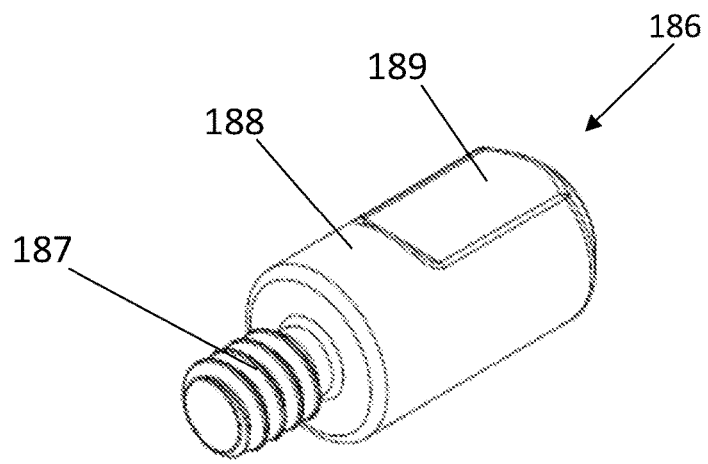
FIG. 13B is an enlarged perspective view of a distal tip of the handle of FIG. 13A.

Valve holder 105 may be used in combination with a handle such as handle 180 shown in FIG. 13A according to an embodiment of the disclosure. Handle 180 may be coupled to the assembled valve holder 105 to manipulate and/or position prosthetic heart valve assembly 100 and to modify the configuration of prosthetic heart valve 10, e.g., deflect the stent posts of the valve medially (i.e., radially inward). Handle 180 includes an elongate proximal grip portion 182, an elongate intermediate shaft portion 184 and a distal end portion 186. Grip portion 182 may be made of plastic and may be shaped to facilitate comfortable and secure holding in one hand of the user. Shaft portion 184 may be made of metal, which may be malleable if it is desired to enable the user to bend the handle laterally if needed. Distal portion 186 includes a generally cylindrical body 188 and a threaded tip 187 having diameter smaller than the cylindrical body, as more clearly shown in FIG. 13B. The smaller diameter of threaded tip 187 creates a surface at the end of body 188 coupled to the threaded tip that may mate with a corresponding surface of valve holder 105 when assembled thereto. A pair of opposing flat surfaces 189 on body 188 provide for an appropriately sized wrench or other instrument to engage distal portion 186 for tightening handle 180 to, or loosening the handle from, valve holder 105.

In a process for assembling valve holder 105 and mounting it to prosthetic heart valve 10, base 110 and spool 130 may be coupled to one another by positioning plug 120 in aperture 111 from one side of the base and coupling it to the spool on the other side of the base. As described above, plug 120 may be coupled to spool 130 such that they are fixed relative to one another, but may be rotated in unison relative to base 110. Base assembly 108 (i.e., base 110, spool 130 and plug 120) may then be coupled to prosthetic heart valve 10 by the suturing process described above. An assembled button housing 140 (i.e., including button 144 and spring 142 positioned therein, as shown in FIG. 11) may then be snapped in place on spool 130 by inserting head 132 of the spool into aperture 146 of receiver 141 pushing the components toward one another until frame 162 of button 144 is captured in the recess of the head as described more fully above. Head 132 may have a transverse shape (e.g., hexagonal or the like) corresponding to that of aperture 165 of button 144 and to that of aperture 146 of receiver 141 such that button housing 140 fits securely over spool 130. The above-described assembly may then be inserted into a storage unit, such as a jar with a lid liner and a cap sealed to the jar, for safe and clean storage and transportation of prosthetic heart valve assembly 100.

Figure 14:
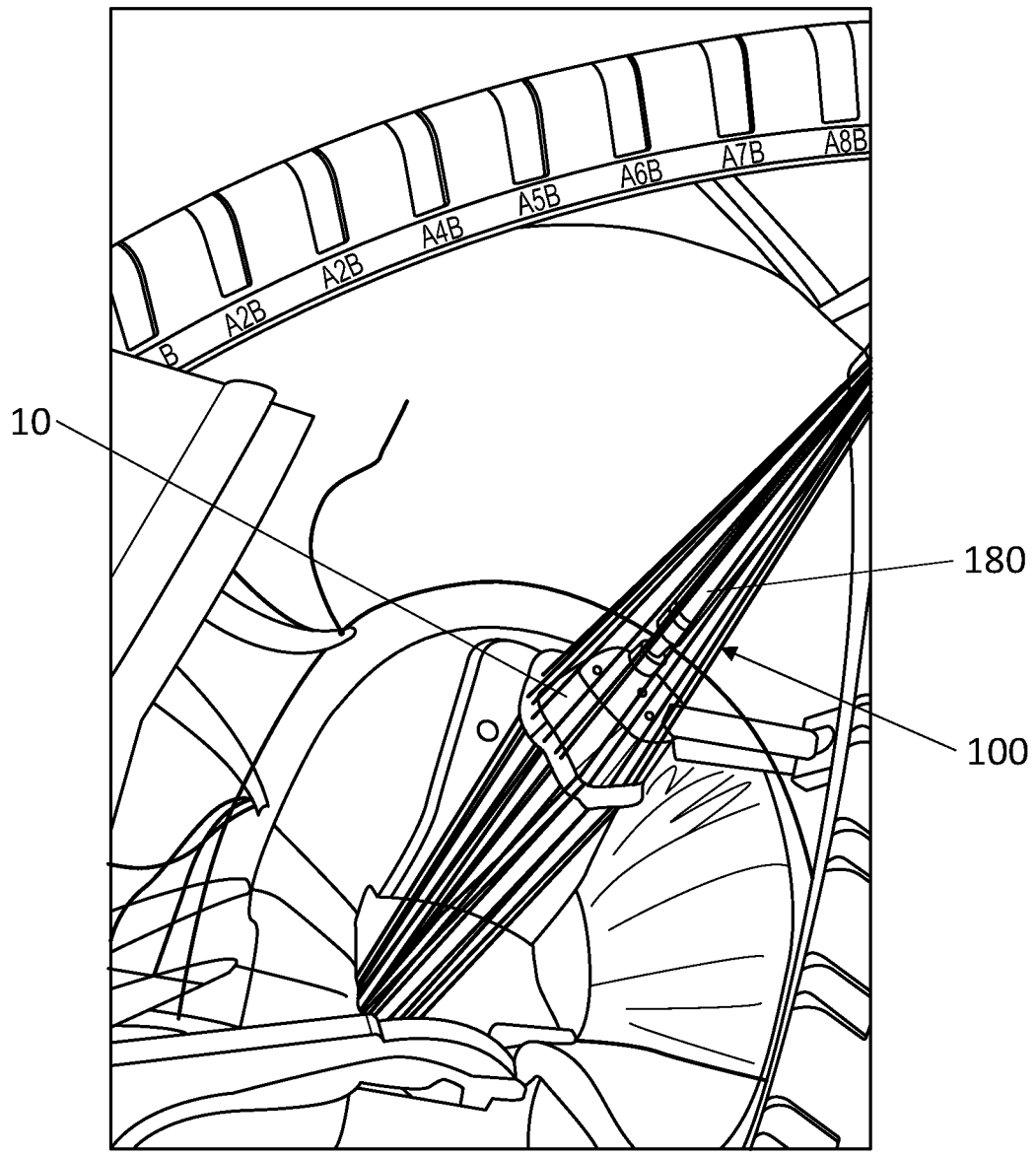
FIG. 14 is a schematic perspective view of a prosthetic heart valve and holder assembly being inserted into a native valve annulus.

When prosthetic heart valve assembly 100 is ready for use, a user may open the jar and assemble handle 180 to the proximal end of valve holder 105, as shown in FIG. 1. Handle 180 may be coupled to valve holder 105 by rotating the handle in a clockwise direction about longitudinal axis X to threadedly engage the threaded distal tip 187 of distal end portion 186 with the corresponding threaded portion of button housing 140 located within the lumen of hollow stem 145. Rotation may continue until the distal tip 187 of handle 180 reaches a distal end of the corresponding threaded portion in button housing 140. Handle 180 may then be further rotated (e.g., further in the clockwise direction) to engage a ratcheting mechanism in which button housing 140, spool 130 and plug 120 rotate relative to base 110, wherein protrusions on the outer perimeter of spool 130 or plug 120 engage ridges 116 in the annular portion 112 of base 110 to prevent counter-rotation. Due to the positioning of lengths of suture 152, 154, 156 described above, rotation of spool 130 may tighten the sutures, causing them to deflect stent posts of valve 10 medially (e.g., radially inward) to promote ease of annulus seating for a user to suture sewing cuff 15 of prosthetic heart valve 10 to the native valve annulus. Prior to implanting prosthetic heart valve assembly 100, additional sutures may be coupled at a first end to the patient's native annulus, and at a second end to sewing cuff 15 of prosthetic heart valve 10, such that the valve assembly may travel along the sutures and parachute down into position within the native valve annulus, as shown, for example, in FIG. 14. The user may grasp valve holder 105 anywhere along the assembly, particularly along handle 180, to translate prosthetic heart valve assembly 100 along the sutures and manipulate the valve into the desired position within the native valve annulus.

Once prosthetic heart valve 10 is properly positioned in the native valve annulus, valve holder 105 may be removed, e.g., in steps or phases. The user may actuate (e.g., press) button 144 to an unlocked configuration by applying a force to actuator portion 164 of the button with a finger, a tool or the like. The force may be applied toward button housing 140 such that button 144 translates deeper into the button housing, overcoming the biasing force of spring 142. At this position, aperture 165 of button 144 may align with the overhang 132a portion of head 132 of spool 130, which may allow button housing 140 and handle 180 to be decoupled and removed from the spool, leaving only base assembly 108 and prosthetic heart valve 10 in the native valve annulus. Removal of handle 180 and button housing 140 may improve the visibility of sewing cuff 15 and the native annulus for a surgeon, thus promoting the ease and effectiveness of securing sewing cuff 15 of valve 10 to the native annulus with sutures. When valve 10 has been sutured to the native valve annulus, first length of suture 152, second length of suture 154 and third length of suture 156 may each be cut, either one at a time or simultaneously within the notch 133 of spool 130. A single cutting region may promote the ease and efficiency of the procedure for removing base assembly 108. Because each length of suture is coupled to valve holder 105 at both ends, cutting the lengths of suture will separate each length of suture into two strands, each strand having a first free end and a second end anchored to the valve holder. Therefore, after the sutures have been cut, lengths of suture 152, 154, 156 decouple and are removed from the valve as base assembly 108 is removed, leaving behind the implanted prosthetic heart valve.

To summarize the foregoing, the present disclosure describes a holder for a prosthetic heart valve including a base having an annular portion defining an aperture; a spool including a platform and a head extending in a longitudinal direction from the platform, the spool being rotatably mated with the base; a button housing having an aperture sized and shaped to receive the head of the spool, the button housing being detachably coupled to the spool in an assembled condition; and a button inserted into the button housing, the button having a button aperture sized and shaped to receive the head of the spool; and/or the head of the spool may have a hexagonal transverse cross-section, and the button aperture may have a hexagonal shape corresponding to the transverse cross-section; and/or the head of the spool may include an interference surface extending transverse to the longitudinal direction, and the button in a locked condition may contact the interference surface to secure the button housing to the spool; and/or the button may be movable in a direction transverse to the longitudinal direction to an unlocked condition in which the button does not contact the interference surface; and/or the button housing may be removable from the head of the spool in the unlocked condition; and/or the button housing in the assembled condition may confront a face of the platform of the spool, and the face of the platform may include a partial impression forming a space between the spool and the button housing; and/or the button housing in the assembled condition may confront a face of the platform of the spool, and the face of the platform may include a ramp forming an open space between the spool and the button housing; and/or the ramp may have a thickness that decreases as the ramp extends radially outward from the head of the spool to an outer edge of the platform; and/or the platform may have an aperture aligned in the longitudinal direction with the head of the spool; and/or the platform may include a notch on an outer edge of the platform, and the holder may further include a plurality of suture lengths extending across the notch; and/or the head of the spool may have an outer surface and a rib projecting radially outward from the outer surface; and/or the rib may be oriented in the longitudinal direction; and/or the button housing may include a hollow stem defining a lumen with a threaded surface on the interior of the hollow stem.

The present disclosure further describes a kit for a prosthetic heart valve assembly including a prosthetic heart valve having a frame extending circumferentially about a longitudinal axis and surrounding a central opening, a plurality of valve leaflets disposed in the central opening and affixed to the frame, each adjacent pair of the leaflets together defining a commissure, and a sewing cuff affixed to the frame and extending circumferentially about an exterior of the frame; a prosthetic heart valve holder including a base having an annular portion defining an aperture, a spool rotatably connectable to the base, the spool including a platform and a head extending from the platform, and a button housing having an aperture sized and shaped to receive the head of the spool, the button housing being detachably couplable to the spool; and a handle connectable to the button housing of the prosthetic heart valve holder, the handle being releasable from the prosthetic heart valve assembly in combination with the button housing; and/or the handle may have a distal threaded tip and the button housing may have a threaded portion for threaded engagement with the distal threaded tip; and/or the kit may further include three lengths of suture coupling the prosthetic heart valve to the prosthetic heart valve holder, the three lengths of suture extending together from a suture anchor on the platform across a notch in an outer edge of the platform to a suture aperture in the platform.

The present disclosure further describes a method of implanting a prosthetic heart valve in a patient including coupling a handle to a first portion of a prosthetic heart valve assembly by rotating the handle relative to the prosthetic heart valve assembly, the prosthetic heart valve assembly including a prosthetic heart valve and a holder coupled to the prosthetic heart valve by a plurality of sutures, the prosthetic heart valve having a frame, a plurality of leaflets joined to the frame, and a sewing cuff surrounding the frame, and the holder including the first portion of the prosthetic heart valve assembly that is releasable from a remainder of the prosthetic heart valve assembly; further rotating the handle relative to the prosthetic heart valve assembly to deflect the frame of the prosthetic heart valve; positioning the prosthetic heart valve in a native heart valve annulus of the patient; decoupling the handle and the first portion of the prosthetic heart valve assembly from the remainder of the prosthetic heart valve assembly; suturing the sewing cuff of the prosthetic heart valve to the native heart valve annulus; cutting the plurality of sutures at a single location to decouple the holder from the prosthetic heart valve; and removing the holder from the patient; and/or the decoupling step may occur prior to the suturing step; and/or the cutting step may include cutting the plurality of sutures with a single cut; and/or the first portion of the prosthetic heart valve assembly may have a locked condition in which the first portion of the prosthetic heart valve assembly is not removable from the remainder of the prosthetic heart valve assembly and an unlocked condition in which the first portion of the prosthetic heart valve assembly is removable from the remainder of the prosthetic heart valve assembly, and the decoupling step may include actuating a button to move the first portion of the prosthetic heart valve assembly from the locked condition to the unlocked condition.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A holder for a prosthetic heart valve, comprising:
a base having an annular portion defining an aperture;
a spool including a platform and a head extending in a longitudinal direction from the platform, the spool being rotatably mated with the base;
a button housing having an aperture sized and shaped to receive the head of the spool, the button housing being detachably coupled to the spool in an assembled condition; and
a button inserted into the button housing, the button having a button aperture sized and shaped to receive the head of the spool.

2. The holder of claim 1, wherein the head of the spool has a hexagonal transverse cross-section, and the button aperture has a hexagonal shape corresponding to the transverse cross-section.

3. The holder of claim 1, wherein the head of the spool includes an interference surface extending transverse to the longitudinal direction, and the button in a locked condition contacts the interference surface to secure the button housing to the spool.

4. The holder of claim 3, wherein the button is movable in a direction transverse to the longitudinal direction to an unlocked condition in which the button does not contact the interference surface.

5. The holder of claim 4, wherein the button housing is removable from the head of the spool in the unlocked condition.

6. The holder of claim 1, wherein the button housing in the assembled condition confronts a face of the platform of the spool, the face of the platform including a partial impression forming a space between the spool and the button housing.

7. The holder of claim 1, wherein the button housing in the assembled condition confronts a face of the platform of the spool, the face of the platform including a ramp forming an open space between the spool and the button housing.

8. The holder of claim 7, wherein the ramp has a thickness that decreases as the ramp extends radially outward from the head of the spool to an outer edge of the platform.

9. The holder of claim 1, wherein the platform has an aperture aligned in the longitudinal direction with the head of the spool.

10. The holder of claim 1, wherein the platform includes a notch on an outer edge of the platform, the holder further including a plurality of suture lengths extending across the notch.

11. The holder of claim 1, wherein the head of the spool has an outer surface and a rib projecting radially outward from the outer surface.

12. The holder of claim 11, wherein the rib is oriented in the longitudinal direction.

13. The hold of claim 1, wherein the button housing includes a hollow stem defining a lumen with a threaded surface on the interior of the hollow stem.

* * * * *